| United States Patent [19] | [11] 3,968,123 |
|---|---|
| Dingwall et al. | [45] July 6, 1976 |

[54] (3-THIOXO-1,2-DITHIOL-4-YL) SUBSTITUTED TRIARYL PHOSPHATES AND THIOPHOSPHATES

[75] Inventors: John Grey Dingwall, Brooklands Sale; Donald Richard Randell, Stockport, both of England

[73] Assignee: Ciba-Geigy Corporation, Ardsley, N.Y.

[22] Filed: June 17, 1974

[21] Appl. No.: 479,937

[30] Foreign Application Priority Data
June 19, 1973 United Kingdom............... 29161/73

[52] U.S. Cl. ............................ 260/327 C; 252/46.6
[51] Int. Cl.² ......................................... C07D 339/04
[58] Field of Search .................. 260/327 C; 252/46.6

[56] References Cited
UNITED STATES PATENTS

| 2,995,569 | 8/1961 | Hamilton et al. | 260/327 C |
|---|---|---|---|
| 3,345,380 | 10/1967 | Hodgson | 260/327 C |
| 3,364,232 | 1/1968 | Anderson | 260/327 C |
| 3,791,985 | 2/1974 | Eiseman et al. | 252/46.6 |
| 3,844,961 | 10/1974 | Clark | 252/46.6 |

FOREIGN PATENTS OR APPLICATIONS

| 679,871 | 9/1952 | United Kingdom | 260/327 C |
|---|---|---|---|

*Primary Examiner*—Sherman D. Winters
*Attorney, Agent, or Firm*—Charles W. Vanecek

[57] ABSTRACT

Novel (3-thioxo-1,2-dithiol-4-yl)substituted triaylphosphates and thiophosphates are used as additives for lubricating oils. The are prepared by reacting corresponding phosphoryl chlorides with 4-(hydroxy-aryl)-1,2-dithiole-3-thiones.

31 Claims, No Drawings

(3-THIOXO-1,2-DITHIOL-4-YL) SUBSTITUTED TRIARYL PHOSPHATES AND THIOPHOSPHATES

The present invention relates to novel (3-thioxo-1,2-dithiol-4-yl) substituted triaryl phosphates and thiophosphates.

According to the present invention there is provided a compound of the general formula:

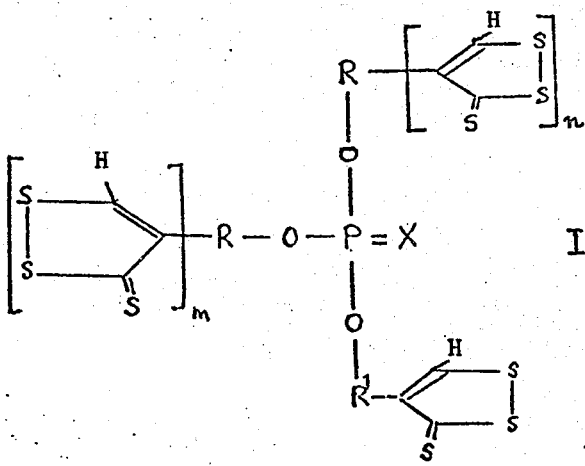

in which X is an oxygen or sulphur atom, R is an aryl or arylene residue containing 6 to 10 carbon atoms and $R^1$ is an arylene residue containing 6 to 10 carbon atoms both R and $R^1$ being unsubstituted or substituted by 1 to 3 branched or straight chain alkyl groups which may be the same or different and may contain 1 to 12 carbon atoms and in which m and n may be 0 or 1.

Preferred compounds of formula I are those in which X is an oxygen atom, R is a phenyl or phenylene residue and $R^1$ is a phenylene residue. When R and $R^1$ are substituted by alkyl groups, these groups preferably contain from 1 to 4 carbon atoms.

The (3-thioxo-1,2-dithiol-4-yl) residue is preferably attached to the aryl or arylene residues R and $R^1$ at the position meta- or para- to the —O-P— linkage.

Examples of the compounds of formula I in which X is an oxygen atom and *m* and *n* are O are as follows:

diphenyl 4-(3-thioxo-1,2-dithiol-4-yl)phenyl phosphate
diphenyl 3-(3-thioxo-1,2-dithiol-4-yl)phenyl phosphate
diphenyl 2-isopropyl-4-(3-thioxo-1,2-dithiol-4-yl)phenyl phosphate
diphenyl 2,6-diisopropyl-4-(3-thioxo-1,2-dithiol-4-yl)phenyl phosphate.
phenyl 2-isopropylphenyl 4-(3-thioxo-1,2-dithiol-4-yl)phenyl phosphate
phenyl 3-isopropylphenyl 4-(3-thioxo-1,2-dithiol-4-yl)phenyl phosphate
phenyl 4-isopropylphenyl 4-(3-thioxo-1,2-dithiol-4yl)-phenyl phosphate
phenyl 2-methylphenyl 4-(3-thioxo-1,2-dithiol-4-yl)phenyl phosphate
phenyl 2-t-butylphenyl 4-(3-thioxo-1,2-dithiol-4-yl)phenyl phosphate
bis (4-isopropylphenyl) 4-(3-thioxo-1,2-dithiol-4-yl)phenyl phosphate
2-isopropylphenyl 3-isopropylphenyl 4-(3-thioxo-1, 2-dithiol-4-yl)phenyl phosphate
2-isopropylphenyl 4-isopropylphenyl 4-(3-thioxo-1,2-dithiol-4-yl)phenyl phosphate
2-isopropylphenyl 4-isopropylphenyl 2-isopropyl-4-(3-thioxo-1,2-dithiol-4-yl)phenyl phosphate
bis (2-methylphenyl) 2-methyl-4-(3-thioxo-1,2-dithiol-4-yl)phenyl phosphate
phenyl 2,4-diisopropylphenyl 4-(3-thioxo-1,2-dithiol-4-yl) phenyl phosphate
2-isopropylphenyl 2,4-diisopropylphenyl 4-(3-thioxo-1,2-dithiol-4-yl)phenyl phosphate
2-isopropylphenyl 2,4,6-triisopropylphenyl 4-(3-thioxo-1,2-dithiol-4-yl)phenyl phosphate
2-methylphenyl 2-methyl-6-isopropylphenyl 4-(3-thioxo-1,2-dithiol-4-yl)phenyl phosphate
2-methylphenyl 2-ethyl-4-isopropylphenyl 4-(3-thioxo-1, 2-dithiol-4-yl)phenyl phosphate Examples of the corresponding thiophosphates where *m* and *n* are O are those listed above but where X is a sulphur atom instead of an oxygen atom. The compound diphenyl-4-(3-thioxo-1,2-dithiol-4-yl)phenyl thiophosphate is an Example.

Examples of compounds of formula I in which X is an oxygen atom, *m* is 1 and *n* is O are as follows:

phenyl bis[4-(3-thioxo-1,2-dithiol-4-yl)phenyl] phosphate
4-isopropylphenyl bis[4-(3-thioxo-1,2-dithiol-4-yl)phenyl] phosphate.
phenyl 3-(3-thioxo-1,2-dithiol-4-yl)phenyl 4-(3-thioxo-1,2-dithiol-4-yl)phenyl phosphate.
phenyl 2-isopropyl-4-(3-thioxo-1,2-dithiol-4-yl)phenyl 4-(3-thioxo-1,2-dithiol-4-yl)phenyl phosphate.
2-methylphenyl bis[2-methyl-4-(3-thioxo-1,2-dithiol-4-yl) phenyl] phosphate.

Examples of the corresponding thiophosphates where *m* is 1 and *n* is O, are those listed above, but where X is a sulphur atom instead of an oxygen atom.

Examples of compounds of formula I in which X is an oxygen atom and m and n are both 1 are as follows:

tris [4-(3-thioxo-1,2-dithiol-4-yl)phenyl] phosphate, and 2-isopropyl-4-(3-thioxo-1,2-dithiol-4-yl)phenyl bis [4-(3-thioxo-1,2-dithiol-4-yl)phenyl] phosphate.

Examples of the corresponding thiophosphates where *m* and *n* are both 1 are those listed above, but where X is a sulphur atom instead of an oxygen atom.

The compounds of the formula I are valuable additives for lubricating oils in which they are ashless antiwear or extreme pressure additives, and antioxidants. They may be added to lubricating oils alone or in admixture with one another or in admixture with triaryl phosphates or in admixture with one another and triarylphosphates, or with 4-(3,5-dialkyl-4-hydroxyphenyl)-1,2-dithiole-3-thiones described in co-pending British Patent Application No. 29334/73. When such compounds of formula I or mixtures described above are dissolved in lubricating oils they impart wear resistant properties to metal surfaces. When the compounds of formula I are used in conjunction with known antioxidants, their antioxidant activity can be enhanced.

The present invention therefore also provides a composition comprising a lubricating oil and a compound having the formula I. The lubricating oil may be a mineral or synthetic oil or may be a mixture of mineral and synthetic lubricating oils, and may, if desired, be in the form of an emulsion. The lubricating oils may contain an amount of the compound of formula I within the range of from 0.001% to 5%, but preferably within the range of from 0.1% to 3% by weight, based on the total weight of lubricating oil.

The lubricating oil may, if desired, contain in addition other additives which are conventionally added to improve the properties thereof, such as antioxidants, metal passivators, rust inhibitors, viscosity index improvers/pour point depressants, dispersants/detergents and other extreme pressure/antiwear additives.

Examples of antioxidants are:
a. Alkylated and non-alkylated aromatic amines and mixtures thereof, for example dioctyldiphenylamine; mono-t-octylphenyl-α and β-naphthylamines; phenothiazine; dioctylphenothiazine; phenyl-α-naphthylamine; N,N'-di-sec-butyl p-phenylenediamine.
b. Hindered phenols, for example 2,6-ditertiarybutyl-p-cresol; 4,4'-bis(2,6-diisopropylphenol); 2,4,6-triisopropylphenol; 2,2'-thio-bis(4-methyl-6-tert-butylphenol); 4,4'-methylene bis(2,6-di-t-butylphenol).
c. Alkyl, aryl or alkaryl phosphites, for example trinonylphosphite; triphenylphosphite; diphenyldecylphosphite.
d. Esters of thiodipropionic acid, for example dilaurylthiodipropionate.
e. Salts of carbamic and dithiophosphoric acids, for example antimony diamyldithiocarbamate, zinc diamyldithiophosphate.
f. Metal salts, and metal complexes of organic chelating agents for example copper bis(trifluoroacetylacetonates), copper phthalocyanines, tributyl ester of ethylenediamine tetra-acetic acid mono sodium salt.
g. Free radical antioxidants for example nitroxides.
h. Combinations of two or more antioxidants from any of the above sections, for example an alkylated amine and a hindered phenol.

Examples of metal passivators are:
a. for copper, for example 1,2,4-triazoles, benzotriazole, 5,5'-methylene-bisbenzotriazole, tetrahydrobenzotriazole, 2,5-dimercaptothiadiazole, salicydene-propylenediamine, salts of salicylaminoguanidine.
b. for magnesium, for example pyridylamines.
c. for lead, for example sebacic acid, quinizarin, propyl gallate.
d. Combinations of two or more of the above additives.

Examples of rust inhibitors are:
a. Organic acids, their esters, metal salts and anhydrides for example N-oleoyl sarcosine, sorbitan mono-oleate, lead naphthenate, dodecenylsuccinic anhydride.
b. Nitrogen containing materials, for example
  i. primary, secondary or tertiary aliphatic or cycloaliphatic amines and amine salts of organic and inorganic acids, for example morpholine, stearyl amine, triethanolamine caprylate.
  ii. heterocyclic compounds, for example imidazolines, oxazolines.
c. Phosphorus containing materials, for example inorganic phosphates, phosphonic acids, amine phosphates.
d. Sulphur containing materials, for example barium dinonylnaphthalene sulphonates.
e. Combinations of two or more of the above additives.

Examples of Viscosity Index Improvers/Pour Point Depressants are, for example:
polyacrylates, polybutenes, polyvinyl pyrrolidones.

Examples of Dispersant/Detergents are, for example:
metal sulphonates (Ca,Ba,Mg) and phenates, polybutenyl succinimides.

Examples of Extreme pressure/Antiwear additives are:
sulphur and/or phosphorus and/or halogen containing materials, for example sulphurised sperm oil, zinc dialkyl phosphoro dithioates, tritolylphosphate, chlorinated paraffins.

The present invention also provides a process of producing compositions of lubricating oils comprising a functionally effective proportion of a compound having formula I, which comprises admixing the lubricating oil with the compound having the formula I.

The compounds of formula I may be prepared by reacting a compound having the formula:

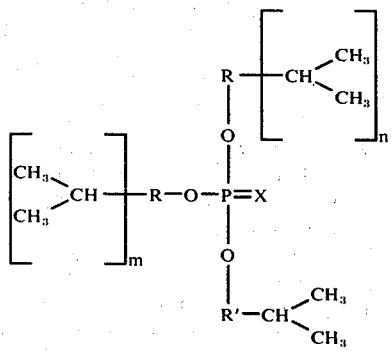

significance with sulphur in a refluxing solvent which is substantially inert to the reactants, in the presence of a basic catalyst.

Suitable solvents are hydrocarbon solvents such as t-butyl benzene and 2,4,6-trimethylbenzene, chlorinated hydrocarbon solvents such as o-dichlorobenzene and dipolar aprotic solvents such as dimethylformamide. Suitable basic catalysts are inorganic bases such as potassium hydroxide and organic bases such as n-amylamine, di-n-amylamine, isoquinoline and guanidines.

Alternatively, the compounds of formula I may be prepared either (1) by reacting a compound having the formula

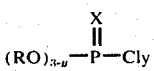

in which R and X have their previous significance and y is an integer from 1 to 3 with a 4-(hydroxyaryl)-1,2-dithiole-3-thione in an inert solvent in the presence of a catalyst or (2) by reacting a compound having the formula

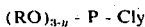

in which R and y have their previous significance with a 4-(hydroxyaryl)-1,2-dithiole-3-thione in an inert solvent in the presence of a catalyst and afterwards reacting with oxygen or sulphur.

Examples of the solvent are xylene, toluene, and o-dichlorobenzene and examples of the catalyst are magnesium turnings, anhydrous magnesium chloride and aluminium chloride. The reaction is preferably carried out at the reflux temperature of the solvent.

The following Example further illustrate the present invention. Parts by weight shown therein bear the same relation to parts by volume as do kilograms to litres. Parts and percentages are expressed by weight unless otherwise stated.

EXAMPLE 1

11.3 parts of 4-(4-hydroxyphenyl)-1,2-dithiole-3-thione and 13.5 parts of diphenyl phosphoryl chloride were heated at reflux for 5½ hours in 200 parts xylene with a catalytic amount of magnesium turnings. The mixture was cooled, the xylene solution decanted, washed with dilute sodium bicarbonate solution and brine, dried and evaporated to yield 19.1 parts of a dark red oil, diphenyl 4-(3-thioxo-1,2-dithiol-4-yl)phenyl phosphate which gave the following elemental analysis:

|  | Required for $C_{21}H_{15}O_4PS_3$ | Found |
| --- | --- | --- |
| Carbon | 55.00 | 55.09 |
| Hydrogen | 3.28 | 3.54 |
| Phosphorus | 6.77 | 6.93 |
| Sulphur | 20.95 | 20.69 |

EXAMPLE 2

7.4 parts of diphenyl 4-isopropylphenyl phosphate and 3.8 parts of sulphur were heated at reflux for 84 hours in 25 parts o-dichlorobenzene, with 0.1 parts of isoquinoline. The o-dichlorobenzene was evaporated and the residue purified by chromatography on a column of silica gel with toluene as eluant, giving 5.8 parts of essentially pure diphenyl 4-(3-thioxo-1,2-dithiol-4-yl)phenyl phosphate, identical (by thin layer chromatography) with the compound prepared in Example 1.

EXAMPLE 3

2.3 parts of 4-(4-hydroxyphenyl)-1,2-dithiol-3-thione and 2.1 parts of phenyl phosphoryl dichloride were heated at reflux for 2½ hours in 80 parts xylene with a catalytic amount of magnesium turnings. A further 2.3 parts of 4-(4-hydroxyphenyl)-1,2-dithiole-3-thione were added and the mixture refluxed a further 2½ hours. The mixture was cooled, the xylene solution decanted and the residue extracted with boiling acetone. The acetone solution was filtered and evaporated to give 3.1 parts of essentially pure phenyl bis [4-(3-thioxo-1,2-dithiol-4-yl)phenyl] phosphate which melted at 75°–80°C and gave the following elemental analysis:

|  | Required for $C_{24}H_{15}O_4PS_6$ | Found |
| --- | --- | --- |
| Carbon | 48.90 | 49.94 |
| Hydrogen | 2.54 | 3.06 |
| Phosphorus | 5.26 | 5.15 |
| Sulphur | 32.50 | 31.22 |

EXAMPLE 4

1.4 parts of 4-isopropylphenol and 2.1 parts of phenyl phosphoryl dichloride were refluxed for 3 hours in 40 parts xylene with a catalytic quantity of magnesium turnings. 2.3 Parts of 4-(4-hydroxyphenyl)-1,2-dithiole-3-thione were then added and the mixture refluxed a further 2 hours. The xylene solution was decanted, evaporated and the residue purified by column chromatography on silica gel with toluene as eluant to give phenyl 4-isopropylphenyl 4-(3-thioxo-1,2-dithiol-4-yl)phenyl phosphate as an orange oil which gave the following elemental analysis:

|  | Required for $C_{24}H_{21}O_4PS_3$ | Found |
| --- | --- | --- |
| Carbon | 57.60 | 57.95 |
| Hydrogen | 4.20 | 4.37 |
| Phosphorus | 6.20 | 6.13 |
| Sulphur | 19.20 | 19.01 |

EXAMPLE 5

8.1 parts of phenyl bis (4-isopropylphenyl) phosphate and 7.8 parts sulphur were refluxed for 118 hours in 50 parts o-dichlorobenzene with 0.1 parts of isoquinoline. The reaction mixture was evaporated and the residue purified by column chromatography on silica gel with toluene as eluant to give an orange oil. Comparison (by thin layer chromatography) of this oil with the compounds prepared in Examples 3 and 4 above showed it to be a mixture of phenyl bis [4-(3-thioxo-1,2-dithiol-4-yl)phenyl] phosphate and phenyl 4-isopropylphenyl 4-(3-thioxo-1,2-dithiol-4-yl)phenyl phosphate.

EXAMPLE 6

A phosphate was prepared by reacting phosphorus oxychloride and a mixture of phenols with the following composition: phenol 30%, o-isopropylphenol 37.5%, m/p-isopropylphenol 13%, 2,4-diisopropylphenol 9%, 2,6-diisopropylphenol 6.5%, 2,5/3,5 diisopropylphenol 2% and 2,4,6-triisopropylphenol 3%. 100 parts of this phosphate, 5 parts of sulphur and 0.3 parts of isoquinoline were heated together for 28 hours at 200°C. Nitrogen was blown through the hot mixture for 2 hours and the mixture was then filtered through a bed of celite. The red oily product contained 2.4% by weight of sulphur.

EXAMPLE 7

A phosphate was prepared by reacting phosphorus oxychloride and a mixture of phenols with the following composition: phenol 20.6%, o-isopropylphenol 13.3%, m/p-isopropylphenol 42%, 2,4-diisopropylphenol 11.8%, 2,5/3,5-diisopropylphenol 10.8% and 2,4,6-triisopropylphenol 0.4%. 100 parts of this phosphate, 10 parts of sulphur and 0.3 parts of iso-quinoline were heated together for 28 hours at 200°C. Work up as described in Example 6 gave a red oily product containing 5.2% by weight of sulphur.

EXAMPLE 8 a. 17.7 parts diphenyl chlorophosphite was added over 40 minutes to a stirred mixture of 15.8 parts 4-(4-hydroxyphenyl)-1,2-dithiole-3-thione and 0.33 parts of aluminium chloride. When the addition was complete the pressure in the reaction vessel was reduced gradually to 20 mm Hg. to remove liberated hydrogen chloride. The temperature was raised to 100°C. over 7 hours when the reaction mass was cooled to room temperature and the vacuum released.

30.9 parts of diphenyl-4-(3-thioxo-1,2-dithiol-4-yl)phenyl phosphite was obtained having the following elemental analysis:

|  | Required for $C_{21}H_{15}O_3PS_3$ | Found |
|---|---|---|
| phosphorus | 7.00 | 7.04 |
| sulphur | 21.74 | 21.82 | b. 30.9 parts diphenyl-4-(3-thioxo-1,2,dithiol-4-yl)phenyl phosphite, 2.2 parts sulphur and 65 parts orthodichlorobenzene were heated at reflux for 6.5 hours. The orthodichlorobenzene was distilled from the reaction mass under reduced pressure. The residue was entracted with acetone which, when the acetone was removed by distillation, yielded 21.6 parts of a red oil.

Preparative thin layer chromatography and Nuclear Magnetic Resonance Spectroscopy showed that the red oil contained 20 to 25% diphenyl-4-(3-thioxo-1,2-dithiol-4-yl)phenyl thiophosphate and 10 to 15% phenyl-bis-[4-(3-thioxo-1,2-dithiol-4-yl)phenyl] thiophosphate.

EXAMPLE 9

10 parts diphenyl p-isopropylphenyl phosphite and 0.91 parts sulphur were heated at reflux in 50 parts orthodichlorobenzene for 16 hours. A further 5.45 parts sulphur and 0.1 part of isoquinoline were then added and the mixture refluxed for a further 96 hours. The orthodichlorobenzene was removed by distillation under reduced pressure and the residue purified by chromatography using an alumina column and toluene as the eluent to give a viscous red oil, whose major component was shown by thin layer chromatography and nuclear magnetic resonance spectroscopy to be identical to the diphenyl-4-(3-thioxo-1,2-dithiol-4-yl)phenyl thiophosphate prepared in Example 8 above.

EXAMPLE 10

The following Example illustrates the use of the compounds of formula I of the present invention as extreme pressure additives for lubricating oils.

The Falex Test, an extreme pressure test for fluid lubricants was carried out in accordance with Method A of the Institute of Petroleum Standards Part I No. 241/69T, but modified to use 100 pound incremental loads containing no additive, one containing a product of Example 1, and two containing a product of Example 6 in the concentrations shown in the following Table I.

TABLE I

| Additive used | Concentration (weight/weight) | Failure Load (lb.) |
|---|---|---|
| None | — | 900 |
| Product of Example 1 | 0.2% | 2000 |
| Product of Example 6 | 0.2% | 1500 |
| Product of Example 6 | 2.0% | 2500 |

EXAMPLE 11

This example illustrates the use of the compounds of formula I as antioxidants.

The CERL Turbine Oil Oxidation test was carried out by incorporating into 25 ml of an 150 Neutral Spindle oil (having a viscosity of 34.9 centistokes at 38°C) 0.5% by weight of a compound of the formula I based on the weight of oil and maintaining the oil at 120°C for 7 days in the presence of metallic copper, oxygen being passed through at a flow rate of 1 liter per hour. The insoluble sludge was filtered off, washed, dried and weighed. The tube was washed with chloroform the chloroform extract evaporated and the residue weighed. The total sludge was thus determined from the two weighings. The acidity increase of the filtered oil was determined potentiometrically and added to the determination of the volatile acidity produced during the test and condensed in 25 ml of water at room temperature. The same procedure was followed twice using the products shown in the following Table II.

TABLE II

| Additive used | Concentration (weight/weight) | % Total sludge | Acid Value increase (mg KoH/g) |
|---|---|---|---|
| None | — | 1.37 | 5.8 |
| Product of Example 1 | 0.5 | 0.95 | 1.7 |
| Product of Example 6 | 0.5 | 1.19 | 3.0 |

We claim:
1. A compound of the formula:

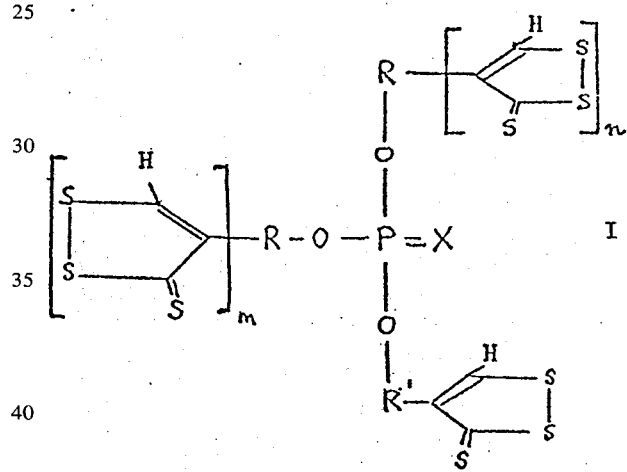

in which X is an oxygen or sulphur atom, R is phenyl or phenylene and $R^1$ is phenylene both R and $R^1$ being unsubstituted or substituted by 1 to 3 branched or straight chain alkyl groups which may be the same or different and may contain 1 to 12 carbon atoms and in which m and n may be 0 or 1.

2. A compound as claimed in claim 1 in which X is an oxygen atom and R is unsubstituted phenylene.

3. A compound as claimed in claim 1 in which R is unsubstituted phenyl or unsubstituted phenylene.

4. A compound as claimed in claim 1 in which when R or $R^1$ are substituted by alkyl groups, these groups contain 1 to 4 carbon atoms.

5. A compound as claimed in claim 1 in which (3-thioxo-1,2-dithiol-4-yl) is attached to the phenyl or phenylene R and $R^1$ at the position meta-or para-to the —O—P— linkage.

6. Compound as claimed in claim 1 which is diphenyl 4-(3-thioxo-1,2-dithiol-4-yl)phenyl phosphate or thiophosphate.

7. Compound as claimed in claim 1 which is diphenyl 3-(3-thioxo-1,2-dithiol-4-yl)phenyl phosphate or thiophosphate.

8. Compound as claimed in claim 1 which is diphenyl 2-isopropyl-4-(3-thioxo-1,2-dithiol-4-yl)phenyl phosphate or thiophosphate.

9. Compound as claimed in claim 1 which is diphenyl 2,6-diisopropyl-4-(3-thioxo-1,2-dithiol-4-yl)phenyl phosphate or thiophosphate.

10. Compound as claimed in claim 1 which is phenyl 2-isopropylphenyl 4-(3-thioxo-1,2-dithiol-4-yl)phenyl phosphate or thiophosphate.

11. Compound as claimed in claim 1 which is phenyl 3-isopropylphenyl 4-(3-thioxo-1,2-dithiol-4yl)phenyl phosphate or thiophosphate.

12. Compound as claimed in claim 1 which is phenyl 4-isopropylphenyl 4-(3-thioxo-1,2-dithiol-4-yl)phenyl phosphate or thiophosphate.

13. Compound as claimed in claim 1 which is phenyl 2-methylphenyl 4-(3-thioxo-1,2-dithiol-4-yl)phenyl phosphate or thiophosphate.

14. Compound as claimed in claim 1 which is phenyl 2-t-butylphenyl 4-(3-thioxo-1,2-dithiol-4-yl)phenyl phosphate or thiophosphate.

15. Compound as claimed in claim 1 which is bis (4-isopropylphenyl)4-(3-thioxo-1,2-dithiol-4-yl)phenyl phosphate or thiophosphate.

16. Compound as claimed in claim 1 which is 2-isopropylphenyl 3-isopropylphenyl 4-(3-thioxo-1,2-dithiol-4-yl)phenyl phosphate or thiophosphate.

17. Compound as claimed in claim 1 which is 2-isopropylphenyl 4-isopropylphenyl 4-(3-thioxo-1,2-dithiol-4-yl)phenyl phosphate or thiophosphate.

18. Compound as claimed in claim 1 which is 2-isopropylphenyl 4-isopropylphenyl 2-isopropyl-4-(3-thioxo-1,2-dithiol-4-yl)phenyl phosphate or thiophosphate.

19. Compound as claimed in claim 1 which is bis (2-methylphenyl)2-methyl-4-(3-thioxo-1,2-dithiol-4-yl)phenyl phosphate or thiophosphate.

20. Compound as claimed in claim 1 which is phenyl 2,4-diisopropylphenyl 4-(3-thioxo-1,2-dithiol-4-yl)phenyl phosphate or thiophosphate.

21. Compound as claimed in claim 1 which is 2-isopropylphenyl 2,4-diisopropylphenyl 4-(3-thioxo-1,2-dithiol-4-yl) phenyl phosphate or thiophosphate.

22. Compound as claimed in claim 1 which is 2-isopropylphenyl 2,4,6-triisopropylphenyl 4-(3-thioxo-1,2-dithiol-4-yl) phenyl phosphate or thiophosphate.

23. Compound as claimed in claim 1 which is 2-methylphenyl 2-methyl-6-isopropylphenyl 4-(3-thioxo-1,2-dithiol-4-yl)phenyl phosphate or thiophosphate.

24. Compound as claimed in claim 1 which is 2-methylphenyl 2-ethyl-4-isopropylphenyl 4-(3-thioxo-1,2-dithiol-4-yl)phenyl phosphate or thiophosphate.

25. Compound as claimed in claim 1 which is phenyl bis [4-(3-thioxo-1,2-dithiol-4-yl)phenyl]phosphate or thiophosphate.

26. Compound as claimed in claim 1 which is 4-isopropylphenyl bis[4-(3-thioxo-1,2-dithiol-4-yl)phenyl]phosphate or thiophosphate.

27. Compound as claimed in claim 1 which is phenyl 3-(3-thioxo-1,2-dithiol-4-yl)phenyl 4-(3-thioxo-1,2-dithiol-4-yl)phenyl phosphate or thiophosphate.

28. Compound as claimed in claim 1 which is phenyl 2-isopropyl-4-(3-thioxo-1,2-dithiol-4-yl)phenyl 4-(3-thioxo-1,2-dithiol-4-yl)phenyl phosphate or hiophosphate.

29. Compound as claimed in claim 1 which is 2-methylphenyl bis [2-methyl-4-(3-thioxo-1,2-dithiol-4-yl)phenyl]phosphate or thiophosphate.

30. Compound as claimed in claim 1 which is tris [4-(3-thioxo-1,2-dithiol-4-yl)phenyl]phosphate or thiophosphate.

31. Compound as claimed in claim 1 which is 2-isopropyl-4-(3-thioxo-1,2-dithiol-4-yl)phenyl bis[4-(3-thioxo-1,2-dithiol-4-yl)phenyl]phosphate or thiophosphate.

* * * * *